United States Patent [19]

Bolich, Jr.

[11] Patent Number: 4,764,363

[45] Date of Patent: Aug. 16, 1988

[54] HAIR STYLING MOUSSE

[75] Inventor: Raymond E. Bolich, Jr., Maineville, Ohio

[73] Assignee: The Procter & Gamble Company, Cincinnati, Ohio

[21] Appl. No.: 874,266

[22] Filed: Jun. 13, 1986

Related U.S. Application Data

[63] Continuation-in-part of Ser. No. 848,415, Apr. 4, 1986, abandoned.

[51] Int. Cl.4 ............................................. A61K 7/00
[52] U.S. Cl. ............................... 424/47; 424/DIG. 1; 424/DIG. 2; 521/70; 521/86; 524/903
[58] Field of Search ............... 424/DIG. 1, DIG. 2, 424/47; 521/70, 86; 524/588, 903, 464, 465, 860

[56] References Cited

U.S. PATENT DOCUMENTS

| | | | |
|---|---|---|---|
| 3,928,558 | 12/1975 | Cheesman et al. | 424/47 |
| 3,964,500 | 6/1976 | Drakoff | 132/7 |
| 4,221,688 | 9/1980 | Johnson et al. | 260/29.2 M |
| 4,450,152 | 5/1984 | Ona et al. | 424/70 |
| 4,505,955 | 3/1985 | Meddaugh | 427/393 |
| 4,529,586 | 7/1985 | DeMarco et al. | 424/70 |
| 4,535,109 | 8/1985 | Kondo et al. | 524/188 |
| 4,597,962 | 7/1986 | Grollier et al. | 424/47 |
| 4,673,568 | 6/1987 | Grollier et al. | 424/47 |
| 4,673,569 | 6/1987 | Shernov et al. | 424/47 |
| 4,680,173 | 7/1987 | Burger | 424/47 |

FOREIGN PATENT DOCUMENTS

| | | |
|---|---|---|
| 0095238 | 11/1983 | European Pat. Off. |
| 2058103 A | 4/1981 | United Kingdom |
| 2143434 A | 2/1985 | United Kingdom |

OTHER PUBLICATIONS

Silicones Product Sheet, General Electric, Mar. 1985.

Primary Examiner—Thurman K. Page
Attorney, Agent, or Firm—Richard C. Witte; Jack D. Schaeffer; Douglas C. Mohl

[57] ABSTRACT

Aqueous aerosol mousse compositions are disclosed which contain a water-dispersible silicone elastomer. The presence of the elastomer provides for clean wet hair feel along with good style retention.

18 Claims, No Drawings

HAIR STYLING MOUSSE

CROSS REFERENCE TO RELATED APPLICATION

This application is a continuation in part of my application U.S. Ser. No. 848,415, filed Apr. 4, 1986 now abandoned.

TECHNICAL FIELD

The present invention relates to aqueous hair styling aerosol mousse compositions which provide excellent set hold as well as combing ease.

BACKGROUND OF THE INVENTION

The desire to have hair (human or other animal) retain a particular shape or configuration is one that is widely held. Approaches taken can either involve permanent alteration of the hair or a temporary alteration. The former involves the use of chemical agents to react with the hair in order to achieve the desired effect. This process can be carried out at either room or elevated temperature.

The temporary set given to hair is, as the term indicates, a temporary arrangement which can be removed by water or by shampooing. The materials used to provide the set have generally been resins or gums. The temporary set compositions have taken the form of gels, lotions and sprays as well as others. The compositions are applied most often to hair dampened with water, combed or by other means spread through the hair and let dry. The set given will vary depending on the materials used.

In recent years a form of a temporary set has been achieved by means of an aerosol foam—a mousse. This form, which can easily be worked through the hair, can provide a set comparable to that given by a gel or a lotion. These products are generally applied to the user's hand and worked through the hair.

The conventional hair styling mousse, which got its start in Europe, generally utilizes a water soluble polymer, water, possibly a conditioning agent, an emulsifier, aesthetic agents and the propellant. The conditoning agents used have included silicone type materials. Such formulations are disclosed in Billek, Doris E., "Aerosol Foam and Mousse Preparations in Europe", *Cosmetics & Toiletries*, Vol. 99 (September 1984), 57-60, 62-67.

The present invention involves the use of a silicone elastomer in combination with other mousse components. The elastomer material is of the type described in U.S. Pat. No. 4,221,688, Sept. 9, 1980 to Johnson et al. The elastomer is a silicone emulsion having a dispersed phase of an anionically stabilized hydroxylated polydiorganosiloxane, colloidal silica, a catalyst and a continuous water phase.

The present invention has found that by including the elastomer material in the mousse formulation a clean wet hair feel is obtained while providing conditoning and styling benefits to dry hair. This is surprising since other silicone materials present in the aqueous phase would likely hurt styling.

Therefore it is a purpose of the present invention to provide a superior hair styling mousse.

It is a further object of the present invention to provide a hair styling mousse employing a water-dispersible silicone elastomer material.

These and other objects of the present invention will become readily apparent from the detailed description which follows.

All percentages and ratios used herein are by weight unless otherwise specified.

SUMMARY OF THE INVENTION

The present invention relates to aerosol compositions comprising water, and silicone elastomer and a propellant phase.

DETAILED DESCRIPTION OF THE INVENTION

The essential as well as optional components are specified below.

WATER

Water, preferably distilled or deionized, is the first essential component of the present invention. The water is generally present at a level of from about 50% to about 95%, preferably from about 80% to about 95% of the total composition.

SILICONE ELASTOMER

The silicone elastomer used in the compositions of the present invention is that type of material described in U.S. Pat. No. 4,221,688 described earlier and incorporated herein by reference. The actual material described in the patent and what is put into the present compositions is an aqueous emulsion which drys to form an elastomer upon removal of water.

The silicone emulsion has a continuous water phase in which there is a dispersed phase which comprises an anionically stabilized hydroxylated polyorganosiloxane, a colloidal silica and a catalyst. The pH of the emulsion should be in the range of from about 9 to about 11.5, preferably from about 10.5 to about 11.2. The solids content of the emulsion is generally from about 20% to about 60%, preferably from about 30% to about 50%. The amount of colloidal silica present for each 100 parts by weight of the polydiorganosiloxane is from 1 to 150 parts. On the same basis the amount of a diorganotindicarboxylate (e.g., dioctyl tindilaurate) catalyst is from 0.1 to 2 parts. The elastomer emulsion is used in an amount of from about 0.1% to about 5%, preferably from about 0.5% to about 2% of the total composition.

PROPELLANT

The agent responsible for expelling the other materials from the container and forming the mousse character is a propellant.

The propellant gas can be any liquefiable gas conventionally used for aerosol containers. Preferably the density of the propellant or mixture thereof is less than 1 so that pure propellant is not emitted from the container. Examples of materials that are suitable for use as propellants are trichlorofluoromethane, dichlorodifluoromethane, dichlorotetrafluoroethane, monochlorodifluoromethane, trichlorotrifluoroethane, dimethylether, propane, η-butane and isobutane, used singly or admixed. The hydrocarbons, particularly isobutane, used singly or admixed with other hydrocarbons, are preferred due to their densities being less than 1.

The amount of the propellant gas is governed by normal factors well known in the aerosol art. For mousses the level of propellant is generally from about 3% to about 30%, preferably from about 5% to about 15% of the total composition. If a propellant such as dimethylether utilizes a vapor pressure suppressant (e.g., trichloroethane or dichloromethane) the amount of suppressant is included as part of the propellant.

OPTIONAL COMPONENTS

A preferred optional ingredient is a hair setting polymer. Any polymer soluble or dispersible in the aqueous phase may be used (if water is the only solvent in the aqueous phase, the polymer should be soluble or dispersible in water; if an optional cosolvent such as ethanol is present the polymer should be soluble or dispersible in the combined solvent system). Solubility/dispersibility is determined at ambient conditions (e.g., temperature about 25° C. and atmospheric pressure). Suitable types of polymers include anionic, nonionic, amphoteric and cationic. Specific polymers include polyvinylpyrrolidone (PVP), copolymers of (PVP) and methylmethacrylate, copolymers of PVP and vinylacetate (VA), polyvinyl alcohol (PVA), copolymers of PVA and crotonic acid, copolymers of PVA and maleic anhydride, hydroxypropyl cellulose, hydroxypropyl guar gum, sodium polystyrene sulfonate, PVP/ethylmethacrylate/methacrylic acid terpolymer and octylacrylamide/acrylate/butylaminoethyl methacrylate copolymers. PVP and PVP copolymers with other monomers are preferred.

Mixtures of polymers may also be used. With certain of the polymers it may be necessary to neutralize some acidic groups to promote solubility/dispersibility (e.g., PVA/crotonic acid).

When present the polymer(s) is used at a level of from about 0.25% to about 15%, preferably from about 1% to about 6% of the total composition. The mass average molecular weight of the polymer is not critical but is generally in the range of from about 2,000 to about 2,000,000.

An optional agent which can provide improved hair conditioning (e.g., dry hair combing) is a high molecular weight silicone material. References disclosing such silicones are U.S. Pat. No. 4,152,416, May 1, 1979 to Spitzer, et al.; *Silicon Compounds,* distributed by Petrarch Systems; and Noll, Walter, Chemistry and Technology of Silicones, New York: Academic Press 1968. Also describing high molecular weight silicone materials are General Electric Silicone Rubber Product Data Sheets SE 30, SE 33, SE 54 and SE 76. These references are incorporated herein by reference.

Because of the ready availability of equipment and the simplicity of the method, commercial manufacturers generally characterize high molecular weight silicones by their viscosity or in some cases by a penetration value. High molecular weight silicone materials denotes polydiorganosiloxanes having a viscosity of at least 100,000 centistokes, preferably from about $10^5$ to about $15 \times 10^6$. Specific examples include polydimethylsiloxane, methylphenyl-diphenyl siloxane copolymer, (polydimethylsiloxane) (methyvinylsiloxane) copolymer and poly(dimethylsiloxane) (diphenyl) (methylvinylsiloxane) copolymer and mixtures of these agents. The silicone material is generally present at a level of from about 0.05% to about 2%, preferably from about 0.1% to about 1% by weight of the total composition. In the present compositions the high molecular weight silicone material may be dissolved in the propellant phase to provide for easier processing or emulsified into the aqueous phase.

Another optional component preferred for use herein is a low viscosity silicone fluid to be used along with the high molecular weight silicone material in the propellant phase. Such materials may be either a polyalkyl siloxane, a polyaryl siloxane, a polyalkylaryl siloxane or a polyether siloxane copolymer. These materials preferably have a viscosity of from about 5 to about 10,000 centistokes, most preferably from about 100 to about 1,000 centistokes, at 25° C. The agent is preferably used at a level of from about 0.1% to about 1% by weight of the total composition.

Another type of preferred optional ingredient is a suspending agent. Useful suspending agents include carboxyvinyl polymers. These are available commercially, e.g., from B. F. Goodrich under the name Carbopol ®. Such polymers are described in U.S. Pat. No. 2,798,053, Brown, issued July 2, 1957, incorporated herein by reference. Also useful are such suspending agents as clays, including bentone, Veegum ® (magnesium aluminum silicate, R. T. Vanderbilt, Inc. ), guar gum and derivatives thereof, xanthan gum, hydroxypropylmethyl cellulose, carboxymethyl cellulose, starches, and mixtures thereof. When present, suspending agents comprise up to about 5% of the composition, preferably from about 0.2% to about 0.5%.

Emulsion stabilizers may also be used in compositions of the invention. Useful examples include, such compounds as polyethylene glycol, silicone copolyols, polyvinyl alcohol, sorbitan monostearate, oleth-2, sorbitan monolaurate, and nonionic block copolymers of ethylene oxide and propylene oxide such as those marketed by BASF Wyandotte under the name Pluronics ®. When present, such stabilizers comprise from about 0.05% to about 1%, preferably from about 0.1% to about 0.8%.

The aerosol mousses herein can also contain a variety of other nonessential, optional components suitable for rendering such compositions more acceptable. Such conventional optional ingredients are well known to those skilled in the art, e.g., other emulsifiers such as anionics (e.g., sodium alkyl sulfate); preservatives such as benzyl alcohol, methyl paraben, propyl paraben and imidazolidinyl urea; cationic emulsifiers/conditioners such as cetyl trimethyl ammonium chloride, stearyldimethyl benzyl ammonium chloride, and di(partially) hydrogenated tallow) dimethylammonium chloride; thickeners and viscosity modifiers such as a diethanolamide of a long chain fatty acid, fatty alcohols (i.e., cetearyl alcohol), sodium chloride, sodium sulfate, and ethyl alcohol; pH adjusting agents such as citric acid, succinic acid, sodium hydroxide and triethanolamine; coloring agents such as any of the FD&C or D&C dyes; hair oxidizing (bleaching) agents such as hydrogen peroxide, perborate salts and persulfate salts; hair reducing agents such as the thioglycolates; perfume oils; chelating agents such as ethylenediamine tetracetic acid; and, among many other agents, polymer plasticizing agents such as glycerin and propylene glycol. These optional materials are generally used individually at a level of from about 0.01% to about 10%, preferably from about 0.5% to about 5% by weight of the total composition.

METHOD OF MANUFACTURE

Methods for making the present compositions are described in Example I and II.

INDUSTRIAL APPLICABILITY

The present compositions are emitted from the aerosol container as a foam which is then worked through the hair with the fingers or a hair styling implement and either left on the hair or rinsed out.

The following Examples further describe and demonstrate the preferred embodiments within the scope of the present invention. The Examples are given solely for the purpose of illustration and are not to be construed as limitations of the present invention as many variations thereof are possible without departing from its spirit and scope.

EXAMPLE I

The following composition was prepared:

|  | Wt. % |
|---|---|
| D.C. Q3-5025 silicone elastomer (40% active)[1] | 1.50 |
| Glydant ®[2] | 0.19 |
| steareth 100 | 0.75 |
| perfume | 0.15 |
| A-46 propellant[3] | 10.00 |
| Double reverse osmosis water | q.s. 100% |

[1]Silicone elastomer offered by Dow Corning
[2]Preservative offered by Glyco Chemical Co.
[3]A mixture of propane (20%), isobutane (78%) and η-butane (2%) offered by Phillips Petroleum Company The aerosol mousses of the present invention are prepared by combining all ingredients except the aerosol propellant into a batch called the concentrate. The concentrate of this example is made by mixing the steareth-100 with agitation in the water for several minutes until there are no lumps. The Glydant and silicone elastomer and perfume are finally added and mixing continued until these are thoroughly dispersed. Aerosol mousse cans are prepared by placing 135 grams of concentrate into 5 oz. alumminum monobloc (epoxy lining) cans, placing mousse valves on can tops, drawing a vacuum to evacuate can headspace (to remove air), and crimping the valves into place. The propellant (15 grams) is added by pressure filling through the valve stem.

EXAMPLE II

The following composition was prepared:

|  | Wt. % |
|---|---|
| Luviskol ® VA55E (50% active)[1] | 9.00 |
| Propylene glycol | 2.00 |
| Carbopol ® 934[2] | 0.20 |
| Cocodimethyl amine oxide | 0.25 |
| Aminomethyl propanol | 0.30 |
| Glydant[3] | 0.37 |
| Perfume | 0.10 |
| D.C. Q3-5025 silicone elastomer (40% active)[4] | 2.50 |
| A-46 propellant[5] | 10.00 |
| Double reverse osmosis water | q.s. 100% |

[1]PVP/PVA Copolymer offered by BASF
[2]Carboxyvinyl polymer offered by B. F. Goodrich Co.
[3]Preservative offered by Glyco Chemical Co.
[4]Silicone elastomer offered by Dow Corning
[5]A mixture of propane (20%), isobutane (78%) and η-butane (2%) offered by Phillips Petroleum Company This mousse concentrate is made by slurrying the Carbopol with agitation in the water for several minutes until there are no Carbopol lumps. To this is added the aminomethyl propanol while increasing the agitator speed to accommodate the increase in viscosity accompanying neutralization. Maintaining vigorous agitation, the remaining ingredients except for Glydant and silicone elastomer are added and mixed until well dispersed. The Glydant and silicone elastomer are finally added and mixing continued until these are thoroughly dispersed. The resulting concentrate is very thick with a pH of 8.2. Aerosol mousse cans are prepared as described in Example I.

EXAMPLE III

This is another example of a composition which was prepared.

|  | Wt. % |
|---|---|
| Luviskol K-30[1] (30% active) | 2.00 |
| Xanthan gum | 0.70 |
| Glydant[2] | 0.37 |
| Nonoxynol-14 | 1.00 |
| D.C. Q3-5024 silicone elastomer (40% active)[3] | 1.00 |
| A-70 propellant[4] | 5.00 |
| Double reverse osmosis water | q.s. 100% |

[1]PVP polymer offered by BASF
[2]Preservative offered by Glyco Chemical Company
[3]Silicone elastomer offered by Dow Corning
[4]A mixture of propane and isobutane offered by Phillips Petroleum Company

EXAMPLE IV

The following is another representative composition which was prepared

|  | Wt. % |
|---|---|
| Amphomer ®[1] | 2.75 |
| Glydant[2] | 0.37 |
| Sodium lauryl sulfate (27% active) | 0.93 |
| Aminomethyl propanol | 0.12 |
| Perfume | 0.10 |
| Carbopol 941[3] | 0.20 |
| D.C. Q3-5025 silicone elastomer (40% active) | 1.00 |
| A-46[4] | 7.50 |
| Double reverse osmosis water | q.s. 100% |

[1]Amphoteric polymer offered by National Starch Company
[2]Preservative offered by Glyco Chemical Company
[3]Carboxyvinyl polymer offered by B. F. Goodrich Company
[4]A mixture of propane (20%), isobutane (78%) and η-butane (2%) offered by Phillips Petroleum Company

EXAMPLE V

The following is another composition representative of the present invention

|  | Wt. % |
|---|---|
| Gantrez ® ES 225[1] (50% active) | 4.00 |
| Carbopol 941 | 0.20 |
| Aminomethyl propanol | 0.80 |
| Glydant | 0.37 |
| A-46 | 8.00 |
| D.C. Q3-5024 silicone elastomer (40% active) | 0.50 |
| Double reverse osmosis water | q.s. 100% |

[1]Copolymer of methylvinyl ether/maleic anhydride offered by GAF
[2]Carboxyvinyl polymer offered by B. F. Goodrich Company
[3]A mixture of propane (20%), isobutane (78%) and η-butane (2%) offered by Phillips Petroleum Company

EXAMPLE VI

The following is another composition representative of the present invention:

|  | Wt. % |
|---|---|
| Amphomer[1] | 1.25 |
| D.C. Q3-5024 (40% active) | 1.00 |
| Glydant[2] | 0.19 |
| sodium alkyl sulfate | 0.30 |
| cocodiethanolamide | 0.25 |
| aminomethyl propanol | 0.15 |
| Carbopol 941[3] | 0.20 |
| perfume | 0.15 |
| A-46 propellant[4] | 10.00 |
| Double reverse osmosis water | q.s. 100% |

[1]Amphoteric polymer offered by National Starch
[2]Preservative offered by Glyco Chemical Co.
[3]Carboxyvinyl polymer offered by B. F. Goodrich Co.
[4]A mixture of propane (20%), isobutane (78%) and η-butane (2%) offered by Phillips Petroleum Company

EXAMPLE VII

The following is another composition representative of the present invention:

|  | Wt. % |
|---|---|
| Amphomer[1] | 2.75 |
| D.C. Q3-5024 (40% active) | 1.00 |
| Glydant[2] | 0.19 |
| sodium alkyl sulfate | 0.30 |
| cocodiethanolamide | 0.25 |
| aminomethyl propanol | 0.15 |
| Carbopol 941[3] | 0.20 |
| perfume | 0.15 |
| A-46 propellant[4] | 10.00 |
| Double reverse osmosis water | q.s. 100% |

[1]Amphoteric polymer offered by National Starch
[2]Preservative offered by Glyco Chemical Co.
[3]Carboxyvinyl polymer offered by B. F. Goodrich Co.
[4]A mixture of propane (20%), isobutane (78%) and η-butane (2%) offered by Phillips Petroleum Company

EXAMPLE VIII

The following is another composition representative of the present invention:

|  | Wt. % |
|---|---|
| Amphomer[1] | 2.75 |
| D.C. Q3-5024 (40% active) | 1.00 |
| Glydant$_2$ | 0.19 |
| sodium alkyl sulfate | 0.30 |
| cocodiethanolamide | 0.25 |
| aminomethyl propanol | 0.15 |
| Carbopol 941[3] | 0.20 |
| perfume | 0.15 |
| Double reverse osmosis water | q.s. 100% |
| methyl phenyl diphenyl silicone fluid (100,000 cs) - propellant phase | 0.20 |
| A-46 propellant[4] - propellant phase | 10.00 |

[1]Amphoteric polymer offered by National Starch
[2]Preservative offered by Glyco Chemical Co.
[3]Carboxyvinyl polymer offered by B. F. Goodrich Co.
[4]A mixture of propane (20%), isobutane (78%) and η-butane (2%) offered by Phillips Petroleum Company

What is claimed is:

1. An aerosol hair styling mousse comprising:
   (a) from about 0.1% to about 5% of a anionically stabilized hydroxylated polyorganosiloxane emulsion capable of forming an elastomer;
   (b) from about 3% to about 30% of an aerosol propellant; and
   (c) water.

2. An aerosol composition according to claim 1 wherein the propellant is selected from the group consisting of trichlorofluoromethane, dichlorodifluoromethane, dichlorotetrafluoroethane, monochlorodifluoromethane, trichlorotrifluoroethane, dimethyl ether, propane, isobutane, η-butane and mixtures thereof.

3. An aerosol composition according to claim 1 further comprising a hair setting polymer.

4. An aerosol composition according to claim 3 wherein the hair setting polymer is selected from the group consisting of cationic, amphoteric, nonionic, and anionic polymers.

5. An aerosol composition according to claim 4 wherein the hair setting polymer is selected from the group consisting of polyvinylpyrrolidone, copolymers of polyvinylpyrrolidone and other monomers and mixtures thereof.

6. An aerosol composition according to claim 3 further comprising a high molecular silicone contained in the propellant phase of the composition.

7. An aerosol composition according to claim 5 wherein the silicone elastomer emulsion has a solid content of from about 20% to about 60% and a pH of from about 9 to about 11.5.

8. An aerosol composition according to claim 7 wherein the silicone present in the emulsion has 2 silicone-bonded hydroxyls per molecule.

9. An aerosol composition according to claim 1 further comprising a suspending agent.

10. An aerosol composition according to claim 9 wherein the suspending agent is selected from the group consisting of carboxyvinyl polymers and clay.

11. An aerosol composition according to claim 10 further comprising a hair setting polymer.

12. An aerosol composition according to claim 11 further comprising a high molecular weight silicone in the propellant phase.

13. An aerosol composition according to claim 1 further comprising an anionic or nonionic surface active emulsion stabilizer.

14. A method of styling hair by applying a composition according to claim 1 to said hair.

15. A method according to claim 14 wherein the composition is according to claim 5.

16. A method according to claim 14 wherein the composition is according to claim 8.

17. A method according to claim 14 wherein the composition is according to claim 10.

18. A method according to claim 14 wherein the composition is according to claim 12.

* * * * *